United States Patent
Knuebel et al.

[11] Patent Number: 5,752,984
[45] Date of Patent: May 19, 1998

[54] USE OF 1,2,3,4-TETRAHYDROQUINOXALINES AS OXIDATION DYE PRECURSORS IN OXIDATIVE COLORING FORMULATIONS

[75] Inventors: Georg Knuebel, Duesseldorf; David Rose, Hilden; Horst Hoeffkes, Duesseldorf; Bernd Meinigke, Burscheid, all of Germany

[73] Assignee: Henkel Kommanditgesellschaft auf Aktien, Germany

[21] Appl. No.: 693,078

[22] PCT Filed: Feb. 4, 1995

[86] PCT No.: PCT/EP95/00404

§ 371 Date: Aug. 12, 1996

§ 102(e) Date: Aug. 12, 1996

[87] PCT Pub. No.: WO95/21604

PCT Pub. Date: Aug. 17, 1995

[30] Foreign Application Priority Data

Feb. 12, 1994 [DE] Germany ............ 44 04 564.6

[51] Int. Cl.[6] ..................................... A61K 7/13
[52] U.S. Cl. ..................... 8/409; 8/406; 8/407; 8/423; 8/567
[58] Field of Search ............... 8/404, 405, 406, 8/407, 408, 409, 423, 565, 567; 544/353

[56] References Cited

U.S. PATENT DOCUMENTS

| | | | |
|---|---|---|---|
| 3,597,424 | 8/1971 | Hunter et al. ............... | 260/240.8 |
| 3,630,655 | 12/1971 | Berth et al. ................. | 8/11 |
| 3,690,810 | 9/1972 | Bugaut ........................ | 8/409 |
| 5,089,025 | 2/1992 | Rose et al. ................... | 8/405 |

FOREIGN PATENT DOCUMENTS

| | | |
|---|---|---|
| 1804066 | 9/1969 | Germany . |
| 1956158 | 5/1970 | Germany . |
| 3825212 | 2/1990 | Germany . |
| 4203537 | 9/1993 | Germany . |
| 619476 | 9/1980 | Switzerland . |

OTHER PUBLICATIONS

A. Nose et al., Yakugaku Zasshi 99 (1979) 1240 No Date Available.

"N-Alkylation of Aromatic Amines by Means of Alcohol IV," Miyano et al., Chem. Phar. Bull., vol. 20, pp. 1328-1331, 1972.

"Effects of Structure on the Ease of Electron Removal from o-Phenylenediamines," Nelsen et al. J. Org. Chem., vol. 46, pp. 283-289, 1981.

*Primary Examiner*—Paul Lieberman
*Assistant Examiner*—Caroline L. Dusheck
*Attorney, Agent, or Firm*—Ernest G. Szoke; Wayne C. Jaeschke; Real J. Grandmaison

[57] ABSTRACT

An oxidative coloring composition for coloring human hair cointaining an oxidation dye precursor in a water-containing carrier, wherein the dye precursor comprises 1,2,3,4-tetrahydroquinoxalines corresponding to formula (I):

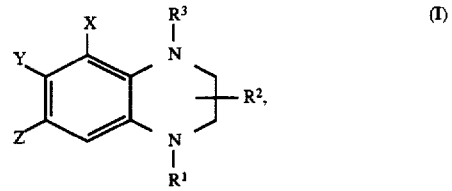

in which $R^1$, $R^2$ and $R^3$ independently of one another represent hydrogen, $C_{1-4}$ alkyl groups, benzyl groups, 2-phenylethyl groups or $C_{2-4}$ hydroxyalkyl groups and X, Y and Z represent hydrogen, fluorine, chlorine, bromine or iodine atoms or $C_{1-4}$ alkyl groups, and wherein at least one of the groups X, Y and Z is hydrogen.

11 Claims, No Drawings

USE OF 1,2,3,4-TETRAHYDROQUINOXALINES AS OXIDATION DYE PRECURSORS IN OXIDATIVE COLORING FORMULATIONS

BACKGROUND OF THE INVENTION

1. Field of the Invention

This invention relates to the use of 1,2,3,4-tetrahydroquinoxalines as oxidation dye precursors in oxidative coloring formulations for coloring keratin fibers, more especially human hair. The 1,2,3,4-tetrahydroquinoxalines are particularly suitable for use a secondary intermediates in conjunction with primary intermediates.

Oxidative coloring formulations normally contain oxidation dye precursors in a water-containing carrier. Primary intermediates and secondary intermediates are used as oxidation dye precursors. The primary intermediates form the actual dyes with one another or by coupling with or more secondary intermediates under the influence of oxidizing agents or atmospheric oxygen.

2. Discussion of Related Art 1,2,3,4-Tetrahydroquinoxalines have never been described as oxidation dye precursors. By contrast, the use of nitro-substituted 1,2,3,4-nitroquinoxalines as substantive dyes is known from DE-A-38 25 212 and from DE-A-42 06 537. It has now been found that specifically substituted 1,2,3,4-tetrahydroquinoxalines are particularly suitable as oxidation dye precursors in oxidative coloring formulations for keratin fibers because they satisfy the requirements oxidation dye precursors are expected to meet (high color intensity of the colors obtained, fastness to light, fastness to washing, fastness to rubbing) particularly effectively. They act as secondary intermediates and differ from conventional secondary intermediates in their orthodiamino functional unit. Secondary intermediates are normally meta-disubstituted aromatic compounds.

DESCRIPTION OF THE INVENTION

The present invention relates to the use of 1,2,3,4-tetrahydroquinoxalines corresponding to formula I:

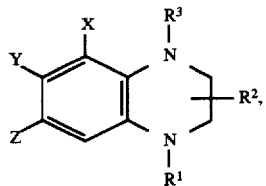

(I)

in which $R^1$, $R^2$ and $R^3$ independently of one another represent hydrogen, $C_{1-4}$ alkyl groups, benzyl groups, 2-phenylethyl groups or $C_{2-4}$ hydroxyalkyl groups and X, Y and Z represent hydrogen, fluorine, chlorine, bromine or iodine atoms, $C_{1-4}$ alkyl groups or $NR^4R^5$ groups, where $R^4$ and $R^5$ independently of one another represent hydrogen, $C_{1-4}$ alkyl groups and $C_{2-4}$ hydroxyalkyl groups, although at least one of the groups X, Y and Z is hydrogen, as oxidation dye precursors in oxidative coloring formulations for coloring keratin fibers. Keratin fibers in the context of the invention are pelts, wool or feathers, but especially human hair.

Particularly preferred 1,2,3,4-tetrahydroquinoxalines corresponding to formula I are those in which $R^2$ and Z are hydrogen, $R^1$ and $R^3$ are hydrogen or $C_{2-4}$ hydroxyalkyl groups and X and Y are methyl groups, chlorine atoms or $NH_2$ groups. 5-Methyl- and 6-methyl-1,2,3,4-tetrahydroquinoxaline are particularly preferred.

The invention includes the salts of 1,2,3,4-tetrahydroquinoxalines corresponding to formula I, the hydrochlorides, hydrobromides and sulfates being mentioned in particular.

Some of the 1,2,3,4-tetrahydroquinoxalines corresponding to formula I are compounds known from the literature which may be synthesized in accordance with the model of the literature references cited in the Examples. Others are new substances which may be obtained from the corresponding quinoxalines or nitroquinoxalines by catalytic hydrogenation. A more detailed description is given in the Examples.

Accordingly, the present invention relates to new 1,2,3,4-tetrahydroquinoxalines corresponding to formula I, at least one of the groups $R^1$ and $R^3$ being a $C_{2-4}$ hydroxyalkyl group.

The present invention also relates to new 1,2,3,4-tetrahydroquinoxalines corresponding to formula I, in which X and Y are both $C_{1-4}$ alkyl groups.

In conjunction with typical primary intermediates, the 1,2,3,4-tetrahydroquinoxalines corresponding to formula I provide a broad spectrum of interesting oxidation dyes ranging from yellow to dark brown in color which, by virtue of their brilliance and favorable fastness properties, are particularly suitable for coloring human hair.

Typical developer components are, for example, primary aromatic amines containing another free or substituted hydroxy or amino group in the para position or ortho position, diaminopyridine derivatives, heterocyclic hydrazones, 4-aminopyrazolone derivatives, 2,4,5,6-tetraaminopyrimidine, 2,4,5-triamino-6-hydroxypyrimidine, 5,6-diamino-2,4-dihydroxypyrimidine and derivatives thereof. Some particularly suitable primary intermediates are mentioned in the Examples.

Accordingly, the present invention relates to oxidative coloring formulations for coloring human hair containing oxidation dye precursors in a water-containing carrier, the 1,2,3,4-tetrahydroquinoxalines corresponding to formula I being present as secondary intermediates in a quantity of 0.05 to 20 mmoles, typical primary intermediates being present in a quantity of 0.05 to 20 mmoles and, optionally, typical substantive dyes being present in a quantity of 0.05 to 20 mmoles per 100 g of the coloring formulation.

In addition to the 1,2,3,4-tetrahydroquinoxalines corresponding to formula I, the hair coloring formulations according to the invention may also contain other known coupler components which are necessary for modifying the hues and for producing natural color tones. Typical secondary intermediates of the type in question are, for example, meta-phenylenediamine derivatives, naphthols, resorcinol derivatives and pyrazolones. Several known primary intermediates and substantive dyes may optionally be used for further modifying the hues. Suitable substantive dyes are, for example nitrophenylenediamines, nitroaminophenols, anthraquinone dyes or indophenols.

The 1,2,3,4-tetrahydroquinoxalines corresponding to formula I need not be individual compounds. Instead, mixtures of various compounds corresponding to formula I may also be used.

In the hair coloring formulations according to the invention, primary intermediates and secondary intermediates are generally used in substantially molar quantities to one another. Although the use of molar quantities has proved to be useful, there is no disadvantage in using a certain excess of individual oxidation dye precursors so that primary intermediates and secondary intermediates may be present in a molar ratio of 1:0.5 to 1:2. To produce the coloring formulations according to the invention, the oxidation dye precursors are incorporated in a suitable water-containing carrier. Suitable carriers are, for example, creams, emulsions, gels or even surfactant-containing foaming solutions, for example shampoos, foam aerosols or other preparations which are suitable for application to the hair.

The water-containing carrier normally contains wetting agents and emulsifiers, such as anionic, nonionic or ampholytic surfactants, for example fatty alcohol sulfates, alkanesulfonates, α-olefin sulfonates, fatty alcohol polyglycol ether sulfates, alkyl glycosides, ethylene oxide adducts with fatty alcohols, with fatty acids, with alkylphenols, with sorbitan fatty acid esters, with fatty acid partial glycerides and fatty acid alkanolamides; thickeners, for example fatty alcohols, fatty acids, paraffin oils, fatty acid esters and other fatty components in emulsified form; water-soluble polymeric thickeners, such as natural gums, for example gum arabic, karaya gum, guar gum, carob bean flour, linseed gums and pectin, biosynthetic gums, for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose, clays, for example bentonite, or fully synthetic hydrocolloids, for example polyvinyl alcohol or polyvinyl pyrrolidone, hair-care additives, for example water-soluble cationic polymers, anionic polymers, nonionic polymers, amphoteric or zwitterionic polymers, pantothenic acid, vitamins, plant extracts or cholesterol, pH regulators, complexing agents and perfume oils and also reducing agents for stabilizing the ingredients, for example ascorbic acid; finally, dyes may also be present for coloring the cosmetic preparations.

The components of the water-containing carrier are used in the usual quantities for the production of the hair coloring formulations according to the invention. For example, emulsifiers are used in concentrations of 0.5 to 30% by weight while thickeners are used in concentrations of 0.1 to 25% by weight, based on the coloring formulation as a whole.

Basically, atmospheric oxygen may be used for oxidative development of the color. However, a chemical oxidizing agent is preferably used, particularly when the hair is to be lightened as well as colored. Suitable oxidizing agents are, in particular, hydrogen peroxide or adducts thereof with urea, melamine or sodium borate and mixtures of such hydrogen peroxide adducts with potassium peroxydisulfate.

The preparation of the oxidizing agent is best mixed with the preparation of the oxidation dye precursors immediately before coloring of the hair. The ready-to-use hair coloring preparation thus formed should preferably have a pH value in the range from 6 to 10. In a particularly preferred embodiment, the hair coloring formulation is applied in a mildly alkaline medium. The application temperatures may be in the range from 15° to 40° C. After a contact time of about 30 minutes, the hair coloring formulation is removed by rinsing from the hair to be colored. There is no need for the hair to be subsequently washed with a shampoo where a carrier of high surfactant content, for example a coloring shampoo, has been used.

The following Examples are intended to illustrate the invention without limiting it in any way.

EXAMPLES

I. Production Examples a. Selected 1,2,3,4-tetrahydroquinoxalines known from the literature 1) 1,2,3,4-Tetrahydroquinoxaline (Beilstein E V 23/6, 24; E III/IV 23/6, 980; E II 23, 106; H 23, 106)
2) 6-Methyl-1,2,3,4-tetrahydroquinoxaline (Beilstein E V 23/6, 59; E III/IV 23/6, 997; E II 23, 107)
3) 6-Chloro-1,2,3,4-tetrahydroquinoxaline (Beilstein E V 23/6, 27; E III/IV 23/6, 985)
4) 6-Amino-1,2,3,4-tetrahydroquinoxaline dihydrochloride (A. Nose et al., Yakugaku Zasshi 99 (1979) 1240)

B. Synthesis of New 1,2,3,4-Tetrahydroquinoxalines 5) 5,6-Dimethyl-1,2,3,4-tetrahydroquinoxaline 5.3 g (0.034 mole) of 5,6-dimethylquinoxaline were dissolved in 200 ml of ethanol and, after the addition of 1 g of Raney nickel, the resulting solution was hydrogenated for 2 h at room temperature/normal pressure. After filtration, the product was concentrated to dryness and recrystallized from methyl-t-butyl ether.

Yield: 3.2 g (59%), Mp.: 72°–73° C.

6) 6-Amino-4-(2-hydroxyethyl)-1,2,3,4-tetrahydroquinoxaline trihydrochloride

A solution of 5 g of 6-nitro-4-(2-hydroxyethyl)-quinoxaline in 80 ml of ethanol was hydrogenated at normal pressure after the addition of 0.5 g of Pd/C (5%). After filtration, dilute hydrochloric acid was added and the product was concentrated to dryness.

Yield: 5.8 g (65%), Mp.: 190° C. (decomp.).

7) 6-Amino-1,4-bis-(2-hydroxyethyl)-tetrahydroquinoxaline trihydrochloride

A solution of 5 g of 6-nitro-1,4-bis-(2-hydroxyethyl)-quinoxaline in 80 ml of ethanol was hydrogenated at normal pressure after the addition of 0.5 g of Pd/C (5%). After filtration, dilute hydrochloride acid was added and the product was concentrated to dryness.

Yield: 3.0 g (46%), Mp.: - (hygroscopic)

8) 6-Amino-4-(2-hydroxypropyl)-1,2,3,4-tetrahydroquinoxaline trihydrochloride

A solution of 5 g of 6-nitro-4-(2-hydroxypropyl)-quinoxaline in 80 ml of ethanol was hydrogenated at normal pressure after the addition of 0.5 g of Pd/C (5%). After filtration, dilute hydrochloric acid was added and the product was concentrated to dryness.

Yield: 5.1 g (78.8%), Mp.: - (hygroscopic)

II. Application Examples

A hair coloring formulation according to the invention was prepared in the form of a hair coloring cream emulsion with the following composition:

| | |
|---|---|
| $C_{12/18}$ fatty alcohol | 10.0 g |
| $C_{12/18}$ fatty alcohol + 2 EO sulfate (Na salt, 28%) | 25.0 g |
| Water | 60.0 g |
| 1,2,3,4-Tetrahydroquinoxaline of formula I according to Examples 1 to 8 | 6.5 mmoles |
| Primary intermediate (PTD, PAP or TAP) | 6.5 mmoles |
| Ammonium sulfate | 1.0 g |
| Conc. ammonia solution | to pH = 9.5 |
| Water | ad 100 g |

PTD: para-tolylenediamine
PAP: para-aminophenol
TAP: tetraaminopyrimidine

The components were mixed together in the listed order. After addition of the oxidation dye precursors and the inhibitor, the pH value of the emulsion was initially adjusted to 9.5 with concentrated ammonia solution, after which the emulsion was made up to 100 g with water.

The color was developed by oxidation either with air or with a 3% hydrogen peroxide solution as oxidizing agent. To this end, 50 g of hydrogen peroxide solution were added to and mixed with 100 g of the emulsion. The coloring cream was applied to approximately 5 cm long tresses of standardized, 90% grey, but not especially pretreated human hair and left thereon for 30 minutes at 27° C. On completion of the coloring process, the hair was rinsed, washed with a standard shampoo and then dried.

Colors Produced by PTD, PAP and TAP with 1,2,3,4-Tetrahydroquinoxalines 1) 1,2,3,4-Tetrahydroquinoxaline:
   PTD: olive
   PAP: olive-brown
   TAP: corn yellow
2) 6-Methyl-1,2,3,4-tetrahydroquinoxaline:
   PTD: dark yellow
   PAP: linoleum brown
   TAP: yellow-brown
3) 6-Chloro-1,2,3,4-tetrahydroquinoxaline:
   PTD: coffee brown
   TAP: corn yellow
4) 6-Amino-1,2,3,4-tetrahydroquinoxaline dihydrochloride:
   PTD: dark brown
   PAP: dark brown
   TAP: olive-brown
5) 5,6-Dimethyl-1,2,3,4-tetrahydroquinoxaline:
   PTD: brown-yellow
   PAP: curry
   TAP: corn yellow
6) Amino-4-(2-hydroxyethyl)-tetrahydroquinoxaline trihydrochloride:
   PTD: dark brown
   PAP: red-brown
   TAP: bronze-brown
7) 6-Amino-1,4-bis-(2-hydroxyethyl)-tetrahydroquinoxaline trihydrochloride:
   PTD: grey-brown
   PAP: brown
   TAP: olive
8) 6-Amino-4-(2-hydroxypropyl)-1,2,3,4-tetrahydroquinoxaline trihydrochloride:
   PTD: dark brown
   PAP: somali
   TAP: sepia

What is claimed is:

1. The process of coloring keratin fibers comprising contacting said fibers with an oxidative coloring composition containing an oxidation dye precursor comprising 1,2,3,4-tetrahydroquinoxalines corresponding to formula (I):

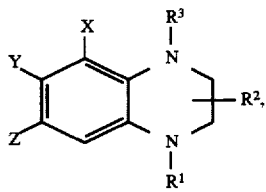

in which $R^1$, $R^2$ and $R^3$ independently of one another represent hydrogen, $C_{1-4}$ alkyl groups, benzyl groups, 2-phenylethyl groups or $C_{2-4}$ hydroxyalkyl groups and X, Y and Z represent hydrogen, fluorine, chlorine, bromine or iodine atoms or $C_{1-4}$ alkyl groups, wherein at least one of the groups X, Y and Z is hydrogen.

2. A process as in claim 1 wherein in said 1,2,3,4-tetrahydroquinoxalines corresponding to formula (I), $R^2$ and Z are hydrogen, $R^1$ and $R^3$ are hydrogen or $C_{2-4}$ hydroxyalkyl groups and X and Y are methyl groups or chlorine atoms.

3. A process as in claim 1 wherein said 1,2,3,4-tetrahydroquinoxalines corresponding to formula (I) comprise 5-methyl- or 6-methyl-1,2,3,4-tetrahydroquinoxaline.

4. A process as in claim 1 wherein in said 1,2,3,4-tetrahydroquinoxalines corresponding to formula (I), at least one of the groups $R^1$ and $R^3$ is a $C_{2-4}$ hydroxyalkyl group.

5. A process as in claim 1 wherein in said 1,2,3,4-tetrahydroquinoxalines corresponding to formula (I), X and Y are both $C_{1-4}$ alkyl groups.

6. An oxidative coloring composition for coloring human hair containing oxidation dye precursors in a water-containing carrier, said dye precursors comprising at least one primary intermediate and at least one secondary intermediate, wherein said secondary intermediate comprises 1,2,3,4-tetrahydroquinoxalines corresponding to formula (I):

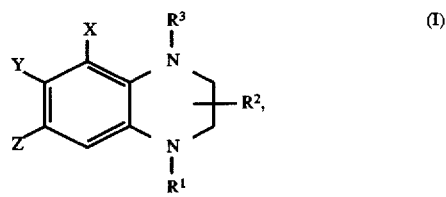

in which $R^1$, $R^2$ and $R^3$ independently of one another represent hydrogen, $C_{1-4}$ alkyl groups, benzyl groups, 2-phenylethyl groups or $C_{2-4}$ hydroxyalkyl groups and X, Y and Z represent hydrogen, fluorine, chlorine, bromine or iodine atoms or $C_{1-4}$ alkyl groups, wherein at least one of the groups X, Y and Z is hydrogen.

7. An oxidative coloring composition as in claim 6 wherein said secondary intermediate is present in a quantity of 0.05 to 20 mmoles and, optionally, substantive dyes present in a quantity of 0.05 to 20 mmoles per 100 g of said coloring composition.

8. An oxidative coloring composition as in claim 6 wherein in said 1,2,3,4-tetrahydroquinoxalines corresponding to formula (I), $R^2$ and Z are hydrogen, $R^1$ and $R^3$ are hydrogen or $C_{2-4}$ hydroxyalkyl groups and X and Y are methyl groups or chlorine atoms.

9. An oxidative coloring composition as in claim 6 wherein said 1,2,3,4-tetrahydroquinoxalines corresponding to formula (I) comprise 5-methyl- or 6-methyl-1,2,3,4-tetrahydroquinoxaline.

10. An oxidative coloring composition as in claim 6 wherein in said 1,2,3,4-tetrahydroquinoxalines corresponding to formula (I), at least one of the groups $R^1$ and $R^3$ is a $C_{2-4}$ hydroxyalkyl group.

11. An oxidative coloring composition as in claim 6 wherein in said 1,2,3,4-tetrahydroquinoxalines corresponding to formula (I), X and Y are both $C_{1-4}$ alkyl groups.

* * * * *